(12) United States Patent
Daf

(10) Patent No.: US 8,597,596 B2
(45) Date of Patent: Dec. 3, 2013

(54) LIQUID HANDLING PLUNGER FOR A BIOLOGICAL SAMPLE IN A TUBE

(75) Inventor: David Daf, Taipei (TW)

(73) Assignee: Taigen Bioscience Corporation, Taipei (TW)

( * ) Notice: Subject to any disclaimer, the term of this patent is extended or adjusted under 35 U.S.C. 154(b) by 0 days.

(21) Appl. No.: 13/611,483

(22) Filed: Sep. 12, 2012

(65) Prior Publication Data
US 2013/0064736 A1 Mar. 14, 2013

(30) Foreign Application Priority Data

Sep. 13, 2011 (TW) .............................. 100132890 A

(51) Int. Cl.
*B01D 35/00* (2006.01)

(52) U.S. Cl.
USPC ........... 422/534; 422/500; 422/501; 422/514; 422/527

(58) Field of Classification Search
USPC .......................... 422/534, 500, 501, 514, 527
See application file for complete search history.

(56) References Cited

U.S. PATENT DOCUMENTS 3,952,782 A * 4/1976 Mannara ....................... 141/100

\* cited by examiner

*Primary Examiner* — Monique Cole
(74) *Attorney, Agent, or Firm* — Hamre, Schumann, Mueller & Larson, P.C.

(57) ABSTRACT

A plunger for mixing a biological sample with a reagent in a tube is moved up and down reciprocally to agitate the biological sample and the reagent for subsequent extraction of the material from the mixture to be analyzed. The plunger's agitation facilitates the concentration of the extracted material to reach an extent where a correct analysis is possible. The plunger of the present invention has a shape of a hollow cylinder with an aperture at the bottom, a plurality of slots formed on the cylindrical surface, and an opening formed at the top. The plunger allows a pipette to draw the extracted material in the test tube out from the opening at the top of the plunger without removing the plunger, and prevents drawing out the fragments of the sample after the biological sample and the reagent have been sufficiently mixed.

6 Claims, 3 Drawing Sheets

LIQUID HANDLING PLUNGER FOR A BIOLOGICAL SAMPLE IN A TUBE

FIELD OF THE INVENTION

The invention relates to a plunger for mixing a biological sample with a reagent in a test tube, in which the plunger is moved up and down reciprocally to sufficiently mix the biological sample with the reagent.

BACKGROUND OF THE INVENTION

In a process of performing biological analysis, biological samples and a reagent are placed in a test tube in order to extract the material to be analyzed. The concentration of the material that is extracted must be in an extent sufficient to be correctly analyzed. For example, when the DNA of a biological sample is to be extracted, normally, the biological sample is placed in a test tube, and subsequently the reagent for extracting the sample is added to mix therewith. In order to effectively extract the DNA, the reagent and the sample must be sufficiently mixed together, such that the concentration of the DNA can be high enough to be analyzed.

Conventionally, a plunger 100 is used for agitation in a test tube 20, vertically and reciprocally, (as shown in FIG. 1) to facilitate mixing the biological sample 102 with the reagent 104. A commonly used plunger is a solid cylinder or a tapered, solid cylinder. When in operation, to avoid the liquid in the test tube from spilling out as the plunger moves reciprocally in the test tube, a sufficiently large gap between the plunger and the test tube is maintained. However, if a gap is too large, the plunger agitation for mixing the sample and the reagent would be less effective.

Moreover, after the extraction process is completed, the extracted material must be drawn out of the test tube for subsequent analysis. Prior to drawing out the material, the plunger must be removed, and a suction pipette 30 is used (as shown in FIG. 2). However, at least two problems will arise during the removal of the plunger. First, the fluid adhered to the plunger may drip outside of the test tube. This not only increases the possibility of the operator's contact with the fluid, but will also contaminate the other test tubes if the fluid drips thereon and causes unanticipated hazardous results. Accordingly, such fluid dripping should be avoided when in the process of handling biological samples. Second, in an automatic process of handling the biological sample, the plunger is removed before the pipette is positioned into the test tube. In this situation, fluid can still drip onto the other test tubes and cause contamination, further complicating the operating process. Additional steps, such as grasping the tubes, removing the plungers, releasing the plungers, are also needed. These additional steps, however, decrease the efficiency of mixing the biological samples with the reagent.

In addition, since a biological sample is obtained by cutting off a chip or a small piece from organisms, the tissue of the sample can be broken into smaller pieces after they are agitated in the test tube. When a suction pipette is used, the sample chips or pieces will be drawn into the suction pipette and cause a blockage.

It is apparent from the above description that the plungers conventionally used still have some drawbacks that need to be overcome.

SUMMARY OF THE INVENTION

The plungers in the present invention have a cylindrical configuration similar to conventional plungers; however, the dissimilarities include the following characteristic features: hollow in the center, an aperture formed at the bottom, a plurality of slots formed on the cylindrical surface, an opening formed at the top, and a shoulder formed around the opening.

When the plungers of the present invention are in use, they are similar to conventional ones, that is, they are moved in the test tube reciprocally to agitate and fracture the biological sample in the test tube, such that the biological sample is sufficiently mixed with the reagent in the test tube, and the material to be analyzed can be extracted.

The plungers of the present invention are hollow. The aperture formed at the bottom of the plunger and the slots formed on the cylindrical surface thereof facilitate to pressure the fluid in the test tube when the plunger is moved downwardly, and part of the fluid will be forced to flow into in the test tube through the aperture and the slots, and the other part of the fluid will be forced to flow through the gap between the test tube and the plunger, and thus produce effective agitation to the fluid in the test tube. After several times of reciprocal movement of the plunger, the sample and the reagent in the test tube can be sufficiently mixed together.

In addition, the plunger of the present invention has an opening at the top thereof, such that after the sample and the reagent in the test tube sufficiently mix together, a suction pipette can be used to draw the fluid mixture within the test tube from out of the opening of the plunger for subsequent analysis. Since the plunger moves up and down reciprocally to agitate the sample and the reagent, the sample will be inevitably fractured into smaller pieces or fragment. If a pipette is used to draw the liquid within the test tube after the plunger is removed, the fragments will very likely be drawn along with the liquid and cause a blockage to the pipette. However, if the pipette is used to draw the liquid from the opening of the plunger, the fragments in the liquid will be excluded from within the plunger and will not be drawn into the pipette.

Accordingly, using the plunger of the present invention will not only shorten the time for mixing the sample and the reagent, but also render the removal of the plunger, before drawing the liquid from the test tube, unnecessary. Thus, the time for mixing the sample with the reagent will be shortened, and contamination due to drippage from the plunger when removed from the test tube can be avoided. In addition, after the sample is mixed with the reagent, the pipette used to draw out the liquid within the test tube will not be blocked by the fragments of the sample.

BRIEF DESCRIPTION OF THE DRAWINGS

The characteristics of the invention will become apparent to those skilled in the art by making reference to the drawings of the invention, along with the following detailed descriptions of the preferred embodiments.

DETAILED DESCRIPTION OF THE PREFERRED EMBODIMENTS

The embodiment of the present invention will be described hereinafter in accordance with the figures.

Figures 3, 4:
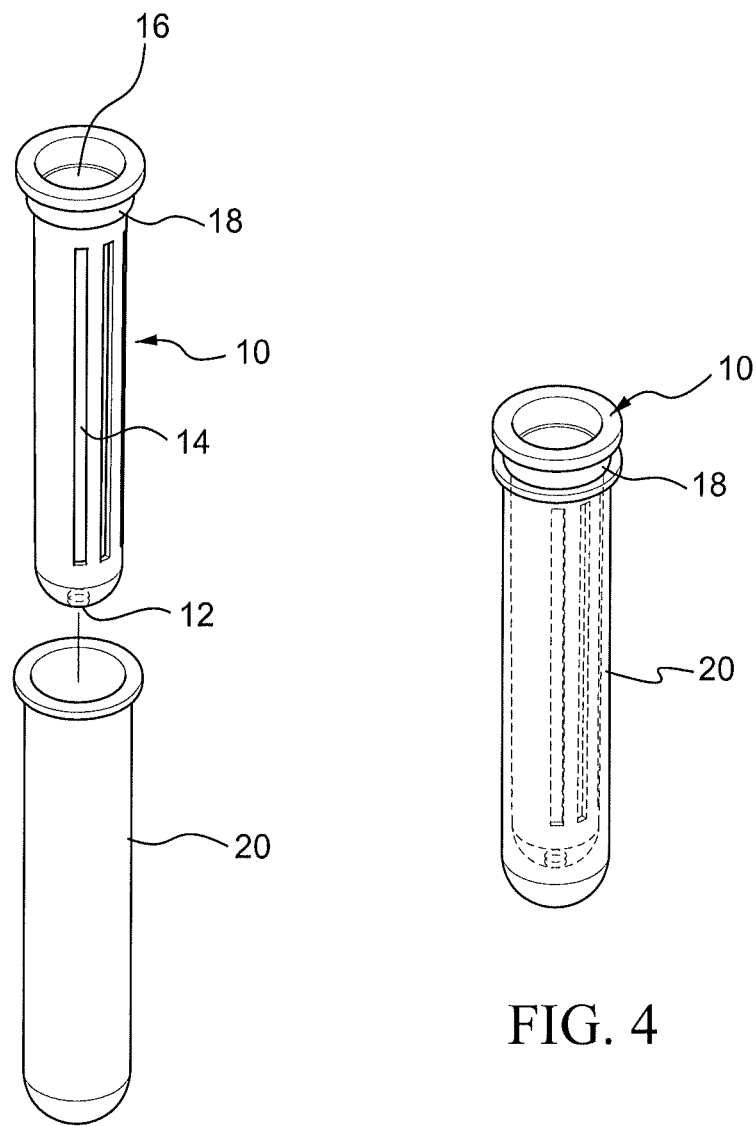
FIG. 3 shows a plunger of the present invention and a test tube used therewith.
FIG. 4 shows the plunger of the present invention completely immersed in a test tube.

The plunger 10 of the present invention is used to facilitate the mixing of a biological sample and a reagent. The plunger is moved up and down reciprocally in a test tube to agitate and fracture the biological sample, such that the biological sample and the reagent are rapidly mixed together. FIG. 3 shows a plunger 10 according to the present invention. The plunger 10 has a cylindrical hollow structure, an opening 16 at top, an aperture 12 at the bottom, and a plurality of slots 14 on the cylindrical surface. Preferably, the slots 14 are formed along the longitudinal axis of the plunger. A shoulder 18 is formed at the top of the plunger 10.

The outer diameter is slightly smaller than the inner diameter of the test tube 20 such that the plunger can move up and down reciprocally in the test tube 20. FIG. 4 shows the state that the plunger 10 is in within the test tube 20. The diameter of the shoulder 18 is larger than the inner diameter of the test tube 20, such that the plunger 10 can rest on the top surface of the test tube 20.

Figure 1:
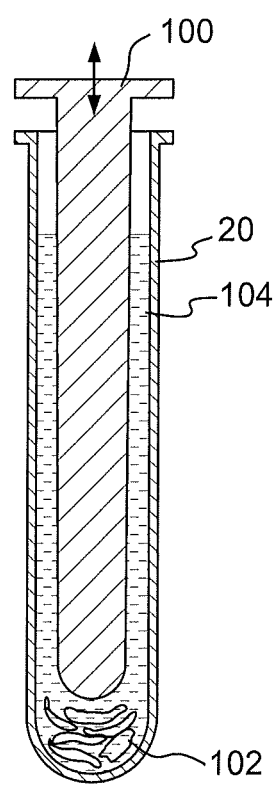
FIGS. 1 and 2 show a plunger used in prior art.
Figure 5:
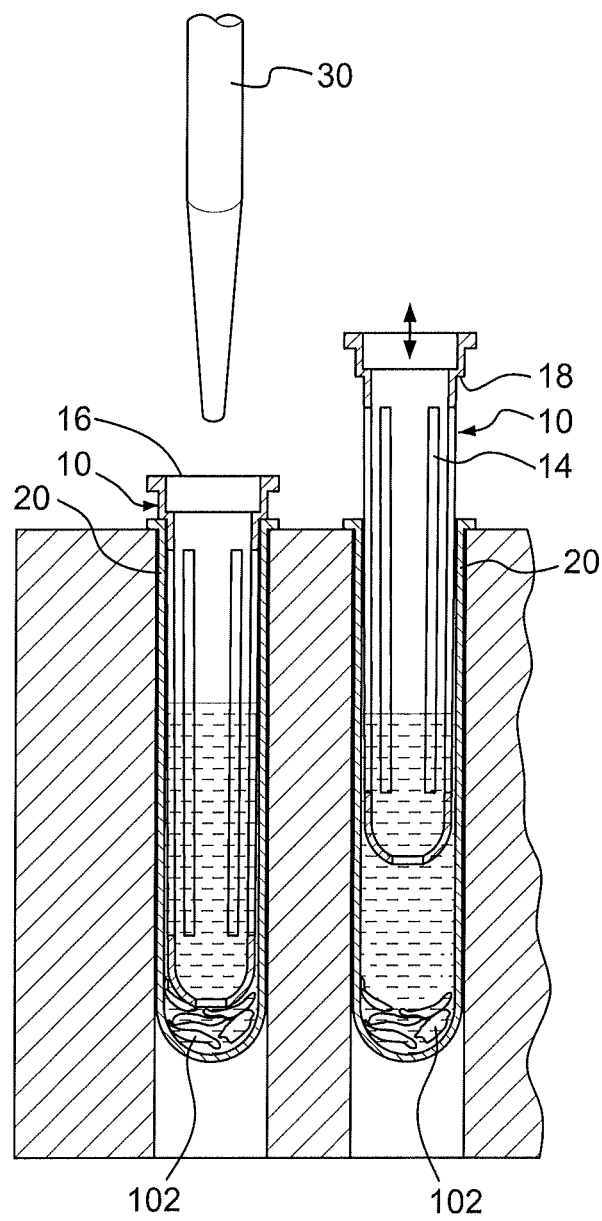
FIG. 5 shows the plunger of the present invention during its operation.

The right side of FIG. 5 shows that the plunger 10 is in the test tube 20 and moves up and down in the test tube 20. The plunger 10 is different from the prior art plunger 100 in FIG. 1. The plunger 10 has a cylindrical shape with a hollow interior. Its bottom has an aperture 12 and its cylindrical surface has a plurality of slots 14. When the plunger is moved downward, the fluid in the test tube 20 is pressed, and a portion of the fluid will flow through the gap between the outer surface of the plunger 10 and the test tube 20. The other portion of the fluid will flow into the interior of the plunger 10 through the aperture 12 and the slots 14. As such, the effect of agitation caused by the plunger surpasses that shown in FIG. 1; that is, the plunger facilitates the extraction of the material from the sample in a much shorter time.

After the agitation and extraction processes are completed, the analysis process begins. As shown on the left side of FIG. 5, the plunger 10 is hollow and has an opening 16 at the top thereof. When the fluid in the test tube 20 is to be drawn out, it is unnecessary to remove the plunger 100, as in the prior art shown in FIG. 2, before positioning the pipette 30 into the test tube 20. As shown on the left side of FIG. 5, the plunger 10 need not be removed. The pipette 30 is directly inserted into the hollow plunger 10 to draw out the liquid therein. Since it is unnecessary to remove the plunger 10, the efficiency of handling the biological sample will be increased. In comparison, when a conventional plunger is removed from the test tube, the liquid adhered to the plunger will drip onto the other test tubes or be contacted by the operator. That not only affects the accuracy of the results of the analysis, but also increases the risk of infection to the operator.

Figure 2:
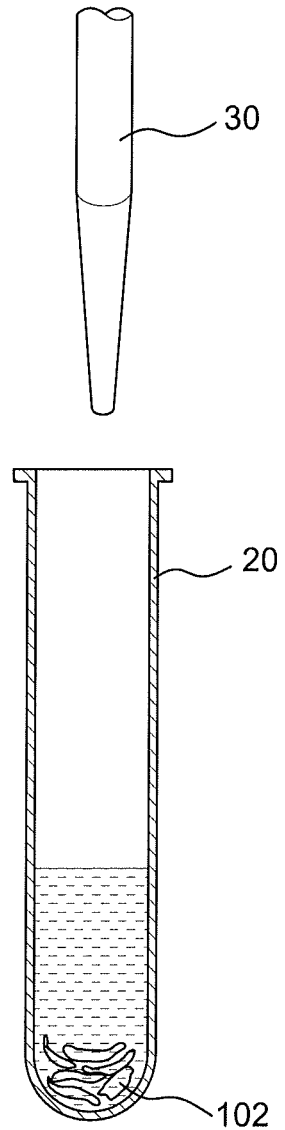

After agitation by the plunger, the test tube normally contains some fragments of the sample 102. If the plunger 100 is removed before a pipette 30 is used to draw out the liquid within the test tube 20 (as shown in FIG. 2), the fragments 102 will inevitably be drawn into the pipette and block the pipette.

As shown on the left side of FIG. 5, after the plunger 10 agitates the sample and the reagent in the test tube 20, the plunger 10 is not removed, but remains positioned in the test tube 20. A pipette 30 is inserted into the test tube 20 through the opening 16 at the top of the plunger to draw out the liquid from therein. As such, the fragments will be obstructed by the plunger 10, and will not be drawn into the pipette 30 to block the pipette 30.

To summarize, the plunger of the present invention has the advantages of performing effective agitation; avoiding test tube spillage; inserting a pipette into a test tube through the opening at the top of the plunger to draw out the liquid within the test tube, without having to first remove the plunger. In addition, since the plunger remains positioned in the test tube, the fragments of the biological sample will be obstructed by the plunger, prevented from entering the pipette when it is used to draw out the liquid within the test tube. Therefore, subsequent analysis of the extracted material will not be interfered with by the fragments drawn out by the pipette.

The invention may also be implemented in other specific modes without departing from the spirit and the essence of the invention. Thus, the above-mentioned embodiment shall be regarded as explanatory but not restrictive. All changes in consistency with the meaning and range of the claims and the equivalents shall fall within the scope claimed by the invention.

What is claimed is:

1. A liquid handling plunger for a biological sample in a tube, the plunger moving up and down reciprocally in the tube, such that the biological sample and reagent in the tube can be sufficiently mixed together; the plunger being hollow in structure with a plurality of slots formed on the surface thereof.

2. The liquid handling plunger of claim 1, wherein the slots are formed along the longitudinal axis of the plunger.

3. The liquid handling plunger of claim 1, wherein an aperture is formed at the bottom of the plunger.

4. The liquid handling plunger of claim 1, wherein an opening is formed at the top of the plunger to allow a pipette to be inserted therein.

5. A plunger configured to be received in a tube for mixing a reagent contained in the plunger with a biological sample contained in the tube, the plunger comprising:
   an elongate plunger body having a top end, a bottom wall and a side wall extending between the top end and the bottom wall, the side wall and the bottom wall defining an internal space;
   a slot defined in the side wall, thereby allowing the internal space and an outside of the plunger to be in fluid communication with each other through the side wall; and
   an aperture defined in the bottom wall of the plunger, thereby allowing the internal space and an outside of the plunger to be in fluid communication with each other through the bottom wall,
   wherein the plunger is configured to prevent fragments disposed in the tube from entering the interior space of the plunger through the aperture.

6. The plunger of claim 5, wherein the plunger is configured to allow fluid to flow into the interior space through the aperture, when the plunger received in the tube moves toward a bottom end of the tube.

* * * * *